United States Patent
Cobb

(10) Patent No.: US 10,131,940 B2
(45) Date of Patent: Nov. 20, 2018

(54) QUANTIFICATION METHODS TO DETERMINE INITIAL TEMPLATE CONCENTRATION BY MEANS OF ASYMMETRIC AMPLIFICATION

(71) Applicant: Epistem Limited, Manchester (GB)

(72) Inventor: Ben Cobb, Manchester (GB)

(73) Assignee: Epistem Limited, Manchester (GB)

( * ) Notice: Subject to any disclaimer, the term of this patent is extended or adjusted under 35 U.S.C. 154(b) by 0 days.

(21) Appl. No.: 15/318,999

(22) PCT Filed: Jun. 29, 2015

(86) PCT No.: PCT/GB2015/051896
§ 371 (c)(1),
(2) Date: Dec. 15, 2016

(87) PCT Pub. No.: WO2016/001641
PCT Pub. Date: Jan. 7, 2016

(65) Prior Publication Data
US 2017/0145491 A1    May 25, 2017

(30) Foreign Application Priority Data
Jun. 30, 2014 (GB) .................................. 1411567.9

(51) Int. Cl.
*C12P 19/34* (2006.01)
*C12Q 1/6851* (2018.01)

(52) U.S. Cl.
CPC .................. *C12Q 1/6851* (2013.01)

(58) Field of Classification Search
CPC ........ C12Q 2531/107; C12Q 2531/101; C12Q 1/6851
USPC ....................................... 435/91.2
See application file for complete search history.

(56) References Cited

U.S. PATENT DOCUMENTS

2006/0057611 A1    3/2006  Kao et al.
2009/0311673 A1*  12/2009  Wittwer ................ B01L 3/5082
                                                                  435/6.12

FOREIGN PATENT DOCUMENTS

WO    WO-03/054233 A1    7/2003
WO    WO-2006/044994 A2  4/2006

OTHER PUBLICATIONS

Zhou et al., Clinical Chemistry 54(10), 1648-1656 (Year: 2008).*
Pierce, K. et al., Linear-After-The-Exponential (LATE)-PCR: Primer design criteria for high yields of specific single-stranded DNA and improved real-time detection, PNAS, 102(24):8609-8614 (2005).
Sanchez, J. et al., Linear-After-The-Exponential (LATE)-PCR: An advanced method of asymmetric PCR and its uses in quantitative real-time analysis, PNAS, 101(7):1933-1938 (2004).

* cited by examiner

*Primary Examiner* — Cynthia B Wilder
(74) *Attorney, Agent, or Firm* — Choate, Hall & Stewart, LLP; Brenda Herschbach Jarrell; Michael L. Vetter

(57) ABSTRACT

Described is a method for quantifying nucleic acid in a nucleic acid amplification reaction, in which an asymmetric nucleic acid amplification reaction is performed on a sample such that double stranded nucleic acid product is generated in an initial stage of the reaction, and single stranded nucleic acid product is generated in a subsequent stage of the reaction once a limiting primer is exhausted. Relative amounts of double stranded nucleic acid product and single stranded nucleic acid product produced are then detected by means of a melt curve analysis. The ratio of double stranded product peak height to single stranded product peak height may then be used to quantify the amount of starting template based on the ratio of double stranded product peak height to single stranded product peak height.

14 Claims, 13 Drawing Sheets

Specification includes a Sequence Listing.

| Copy Number | Peak Height 1/Peak Height 2 | | | | |
|---|---|---|---|---|---|
| | Replicate 1 | Replicate 2 | Replicate 3 | AVE | Comments |
| $1 \times 10^6$ | 3.424729643 | 3.308802039 | 3.309385582 | 3.3473379 | |
| $5 \times 10^5$ | 3.124837806 | 3.113331967 | 3.015699183 | 3.084619 | |
| $2.5 \times 10^5$ | 2.911776081 | 2.8788682 | 2.818094547 | 2.86958 | |
| $1 \times 10^5$ | 2.497193356 | 2.236221 | 2.340090259 | 2.357835 | |
| $5 \times 10^4$ | 1.995777142 | 2.276645447 | 1.887921349 | 2.053382 | |
| $1 \times 10^4$ | | 0.163385407 | 0.135968958 | 0.149912 | Out of quant range |
| NTC | 0 | 0 | 0 | 0 | |
| NTC | 0 | 0 | 0 | 0 | |

Fig 5A

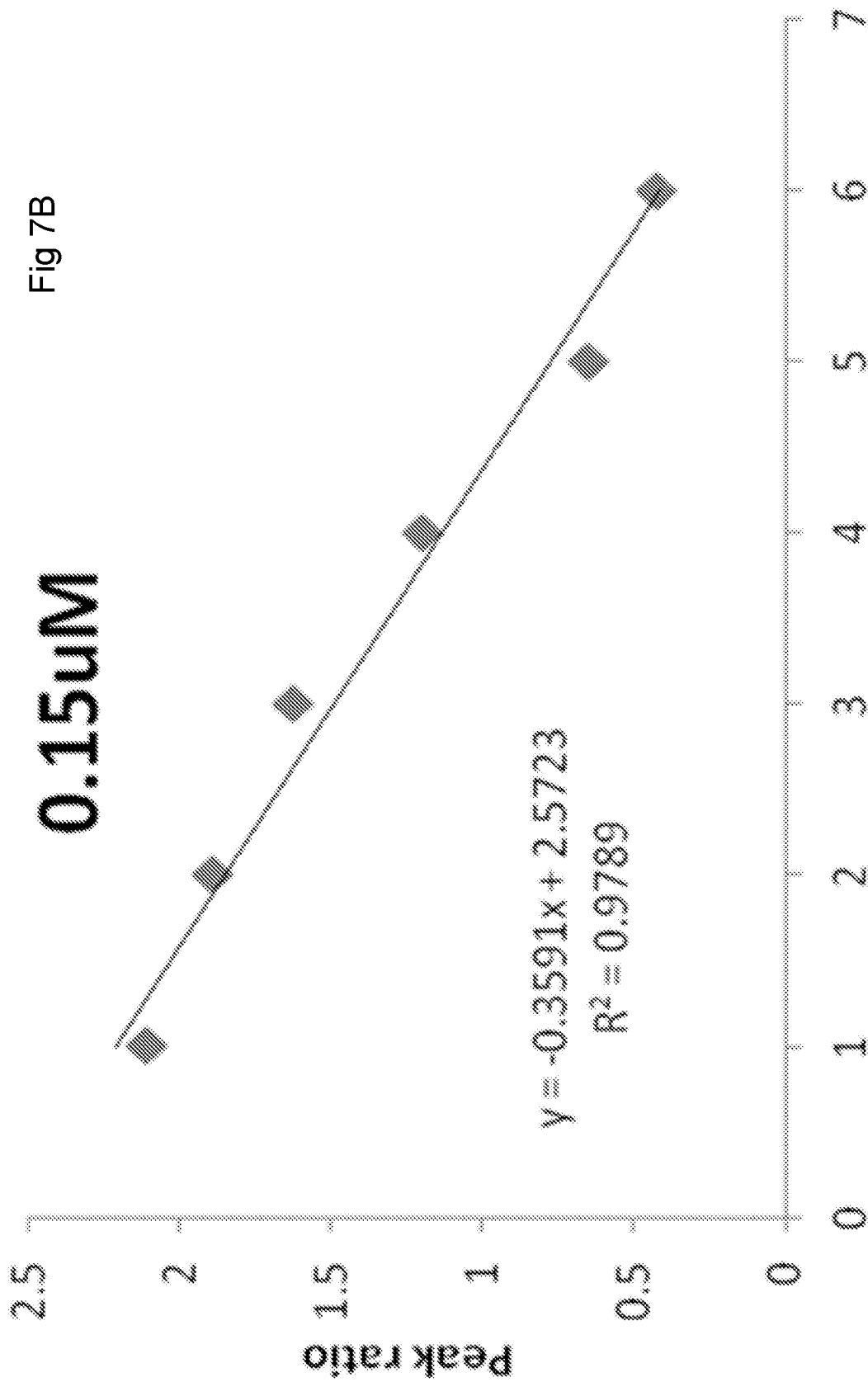

QUANTIFICATION METHODS TO DETERMINE INITIAL TEMPLATE CONCENTRATION BY MEANS OF ASYMMETRIC AMPLIFICATION

FIELD OF THE INVENTION

The present invention relates to a method for quantification of nucleic acids in a nucleic acid amplification reaction.

BACKGROUND OF THE INVENTION

One of the requirements of quantitative PCR is to accurately determine the number of copies of starting template in a given sample, this is generally achieved by measuring the cycle threshold (CT; that is, the number of cycles for measured fluorescence to increase above a predetermined threshold) of the amplification of the unknown and referencing this back to a standard curve of known copy number. A lower CT indicates a greater amount of starting template. Typically the CT is determined as the point where the amplification reaction shifts from the baseline to the exponential amplification stage.

Use of a standard curve is however difficult with diagnostic instruments, where it is generally inconvenient to run such a curve. Further, standard curves can differ from reaction to reaction, depending on the reaction conditions, the presence of certain ions in the sample, etc, so it is considered best practice to use a separate standard curve derived for each reaction. This clearly is impractical for diagnostic assays and more specifically in point of care devices that generally rely on a single reaction.

It is known to use a well-characterized amplification internal to the assay amplification, to measure deviation from known metrics; this is also based on CT measurement from real time data. However, this is not always convenient because the internal control can compete for reaction components, reducing the limit of detection and sacrificing sensitivity.

There is a need for an improved quantification method that is compatible with diagnostic instrumentation. We describe a process that provides quantification metrics as part of the same amplification reaction, which also allows use of melt curve analysis to reduce the complexity of the reaction, providing both quantitative and genotyping information from a single amplification.

SUMMARY OF THE INVENTION

According to the present invention, there is provided a method for quantifying nucleic acid in a nucleic acid amplification reaction, the method comprising:
  providing a template nucleic acid and first and second amplification primers, wherein the first primer is present in a limiting quantity;
  performing an asymmetric nucleic acid amplification reaction under suitable conditions such that double stranded nucleic acid product is generated in an initial stage of the reaction, and single stranded nucleic acid product is generated in a subsequent stage of the reaction once the limiting primer is exhausted;
  providing a probe specific for the single stranded nucleic acid product, and allowing the probe to hybridise to single stranded product;
  detecting relative amounts of double stranded nucleic acid product and single stranded nucleic acid product produced once the reaction has entered the subsequent stage by means of a melt curve analysis;
  determining whether the ratio of double stranded product peak height to single stranded product peak height is less than one; and
  if said ratio is less than one, then quantifying the amount of starting template based on the ratio of double stranded product peak height to single stranded product peak height.

Preferably the nucleic acid is DNA or cDNA.

Asymmetric PCR has two distinct phases. In the first exponential phase there is an exponential doubling of product over successive cycles. As the limiting primer is exhausted, the amplification transitions into one producing single stranded amplicon.

Melt curve analysis at the end of the amplification allows the detection of both the amount of single stranded product and double stranded nucleic acid, thereby allowing generation of two detection peaks. One peak reflects the limiting primer incorporated as part of the double stranded duplex formed during the exponential phase, and one peak is determined due to the probe binding to the single stranded DNA formed as part of the linear phase. The height of the single stranded peak determined after the linear phase is proportional to the quantity of starting template. This alone does not provide sufficient data to quantify the starting template, due to the confounding factors referred to above. However, since the amount of double stranded product is limited (defined by the proportion of limiting primer to excess primer), the maximum amount of double stranded product reaches a threshold at the transition from exponential phase to linear phase, and does not increase beyond that. After the transition phase there is an increasing amount of single stranded template for the probe to bind to and therefore an increasing secondary peak whose height is proportional to starting template quantity. The double stranded peak therefore acts as a defined calibrator or reference from which to measure the height of the single stranded product.

The dsDNA peak can also be used to act as an acceptance or rejection threshold for the secondary peak since its height can only ever reach a maximum threshold, and it can also be used as a known quantity marker to measure the proportional height of the ssDNA peak. That is, if the determined ratio of dsDNA to ssDNA is less than one, then it is an indication that the amplification has reached the threshold; the ratio may be used as a surrogate for CT. If the ratio of dsDNA to ssDNA is greater than one, then the amplification has not reached the transition threshold, and the result cannot reliably be used to quantitate the starting template. Therefore, if said ratio is greater than one, then the method may further comprise discarding the reaction. Alternatively, the method may further comprise continuing the reaction until said ratio is less than one.

The amount of single stranded product may be normalised with respect to the amount of double stranded product; that is, the amount of double stranded product may be predetermined (for example, by using a predetermined amount of the limiting primer), and this known measurement used to determine the amount of single stranded product based on the ratio of double stranded to single stranded product.

The amounts of double stranded and single stranded product are detected by melt curve analysis. In preferred embodiments a detectable label is used; for example, to detect double stranded product, a fluorescent dye which preferentially binds to double stranded nucleic acid may be used. A preferred such dye is SYBR® Green or related dyes.

In other embodiments, the limiting primer itself may be labelled with a detectable label; this allows primer incorporated into the double stranded product to be detected and distinguished. A suitable dye may be a fluorescent label, such as 6-FAM.

The single stranded product is detected by means of a probe specific for a target sequence within the product. The probe may be present within the amplification reaction at the beginning, or may be added subsequent to amplification. The presence of the probe may be detected, and hence the amount of single stranded product determined, by melt curve analysis of the association or dissociation of the probe from the product. The probe may be labeled, for example with a fluorescent label, or a dye specific for double stranded DNA may be used to detect hybridization. In preferred embodiments, the label or dye provides a signal distinct from that of the label or dye used to detect double stranded product.

The method may further comprise the step of predetermining the amount of the limiting primer, to provide a predetermined quantity of double stranded DNA. This may be chosen based on the reaction to be carried out, and may be selected to provide a desired degree of sensitivity to the reaction. For example, below a defined copy number only dsDNA is produced, so the amount of limiting primer may be selected to give a ratio of dsDNA to ssDNA of from 1:15 to 1:5; this ensures that the ratio of products is within a defined range, thereby improving sensitivity of the method and tuning the peak height to a specific threshold.

In certain embodiments of the invention, the probe specific for the single stranded product may be a probe that can be used to distinguish between alleles of a target sequence; for example, alleles of a particular gene present in the starting template. For example, the probe may be such as described in international patent publication WO2012/093262, the contents of which are incorporated herein by reference. That publication describes the use of a probe as a blocking probe to preferentially amplify a mutant allele of a locus, by virtue of the probe hybridising to mutant and wild type alleles with different melting temperatures. A similar probe may be used in the current method, in order to distinguish between alleles of a target gene. In this way, the current method may not only quantify starting template, but also be used to genotype the template. In this embodiment, the probe hybridises to the first allele with a lower melting temperature (Tm) than that with which it hybridises to the second allele; the primers hybridise to the nucleic acid in the sample at first and second sites flanking the oligonucleotide probe binding site; wherein the Tm of the primer: sample is higher than the Tm of the probe: first allele; and the method includes the steps of: maintaining the reaction mix at a temperature between the probe: first allele Tm and the probe: second allele Tm, such that the probe preferentially hybridises to the second allele; carrying out a thermal cycling amplification on the reaction mix, the amplification including a melt phase, an annealing phase, and an extension phase, in which the temperatures of the extension and annealing phases are between the probe: first allele Tm and the probe: second allele Tm, such that the probe is hybridised to the second allele during these phases; to thereby amplify the first allele; and hybridisation of the probe to the sample is detected at a temperature at or below the probe: first allele Tm, and at a higher temperature at or below the probe: second allele Tm.

In a further embodiment of the invention, the probe may be a linker probe such as that described in international application WO2013/041853, the contents of which are incorporated herein by reference. That application describes use of a probe having an anchor region and a reporter region separated by a linker nucleic acid sequence, the anchor and reporter regions having discrete melting temperatures. This probe too may be used to carry out genotyping of targets, where the reporter region is designed to have first and second melting temperatures when hybridised to wild type and mutant allele sequences.

BRIEF SUMMARY OF THE DRAWINGS

These and other aspects of the present invention will now be described by way of example only and with reference to the accompanying drawings in which.

DETAILED DESCRIPTION OF THE DRAWINGS

Figure 1:
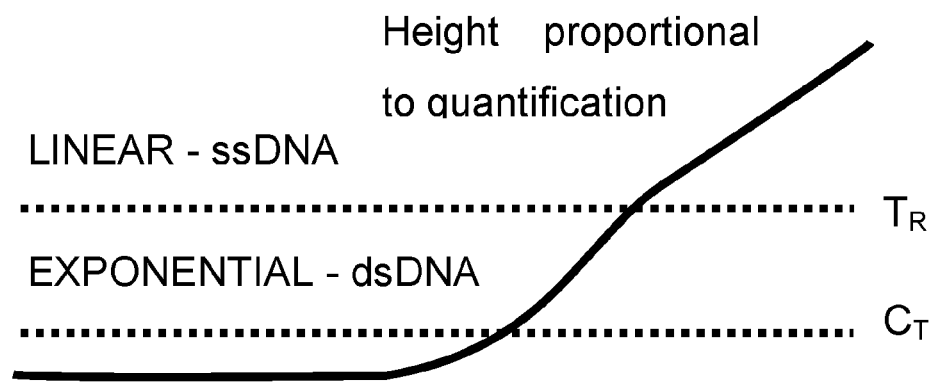
FIG. 1 shows a schematic of amount of DNA in exponential and linear amplification phases of asymmetric PCR.

Referring first of all to FIG. 1, this shows a schematic of the amount of DNA in an asymmetric PCR amplification reaction. The reaction includes a template, and first and second primers, with the first primer being present in limiting amounts. In the initial exponential stage, both primers are present in sufficient amounts to allow doubling of product in successive cycles, and the production of double stranded DNA. Once the limiting primer is exhausted, the reaction transitions into the linear stage in which single stranded amplicon is generated, with a linear rather than exponential increase.

If the limiting primer is labelled using a fluorophore, or if a double strand specific dye such as SYBR® Green is used, then the amount of double stranded product can be readily quantified using melt curve analysis. Addition of a separate probe for the single stranded product—for example, labelled using a second fluorophore—can also be used to quantify the single stranded product. The probe may either be present in the reaction mix, or may be added subsequent to amplification. Further, use of a probe which hybridises with different specificity to distinct target sequences can be used to further analyse the single stranded product. For example, the single stranded product may be assayed by melt curve analysis to distinguish distinct genotypes.

The amount of double stranded product is limited by the amount of limiting primer, such that the maximum quantity of double stranded product is known. This allows the double stranded product to be used to calibrate the determined quantity of single stranded product, or as a reference value to determine the amount of single stranded product from the measured peak height during melt curve analysis.

The primer labelled product can also be used to generate a CT value, which serves as a check on the reaction; in addition, the fluorescence of the single stranded product after the linear phase is proportional to the quantity of starting template.

Figure 2:
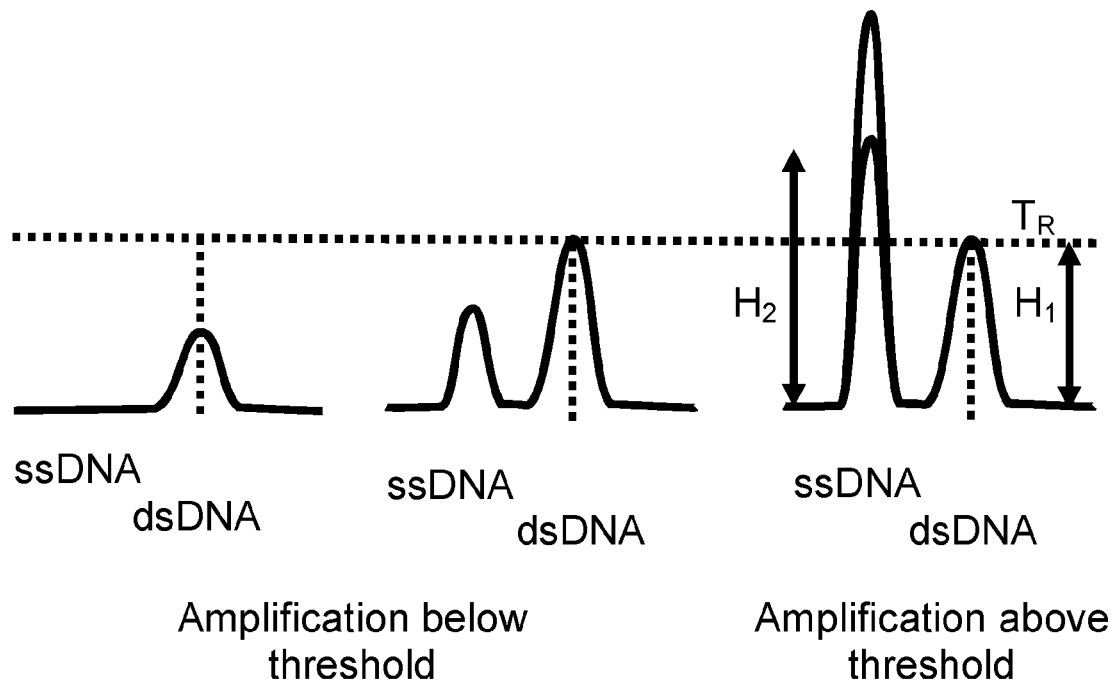
FIG. 2 shows relative peak heights of single and double stranded DNA from sample reactions.

However, since the double stranded product is limited by the amount of limiting primer, this can also be used to check quality of reaction and as an internal control. As shown in FIG. 2, the reaction will produce double stranded product to a maximum amount. This quantity will not increase in subsequent amplification cycles, whereas the single stranded product is not so limited and will continue to increase. Therefore the amplification can be carried out until it is in the linear phase, and the relative quantities of nucleic acid produced can be determined (for example, by determining the heights of peaks in fluorescent melt curve analysis). The dsDNA peak can be used as an acceptance or rejection threshold for the ssDNA peak—if the ratio of the peaks is less than one (ie, there is more ssDNA than dsDNA), then the reaction has proceeded past the transition phase and the amount of ssDNA can be taken as being proportional to the starting template.

By contrast, if the ratio of the peaks is more than one (there is more dsDNA than ssDNA), then the reaction has not proceeded past the transition phase, and the amount of ssDNA cannot be taken as being directly proportional to the starting template. In this case, the assay is rejected as having failed. Alternatively, the reaction may be continued until the ratio of the peaks is less than one.

In this way, the measure of the ratio of H1 (height of dsDNA peak) to H2 (height of ssDNA peak) gives both an internal control to ensure the reaction is complete, and may be used as a known quantity marker if the peak amount of dsDNA is known. This can give an absolute as well as a relative quantification of the amount of starting template. Likewise, the absolute value of H1 (dsDNA) can be used to determine whether the reaction is complete.

Figure 3:
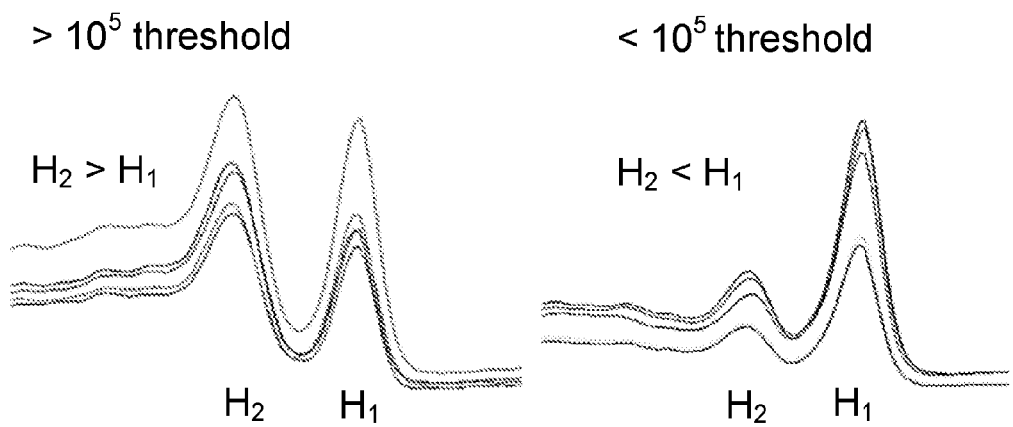
FIG. 3 shows results from a sample assay carried out for *Mycobacterium tuberculosis* in a sample.
Figure 3:
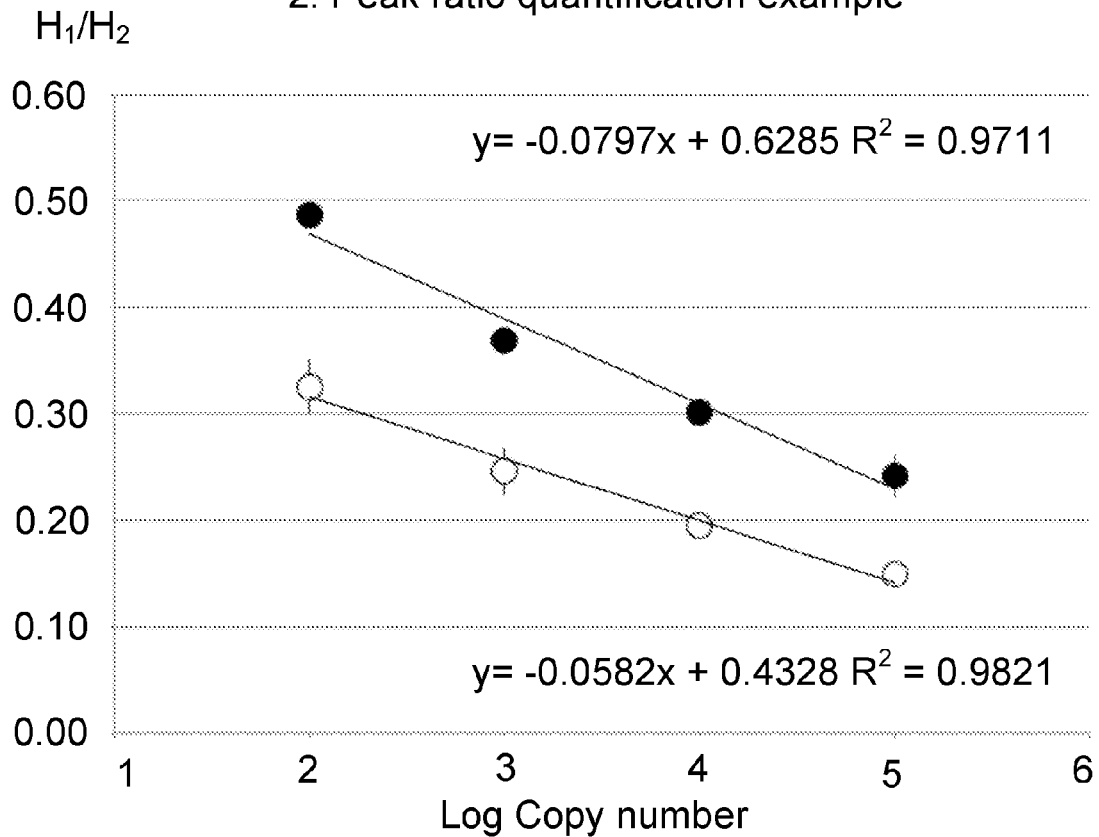

An example of this method is shown in FIG. 3. Using *Mycobacterium tuberculosis* as a model system, one primer was labelled replacing the two Ts with FAM-T, and the other primer unlabelled. A probe specific for the amplified sequence was used to detect amplification.

Reaction conditions and probes and primers were as used in UK patent application GB1317355.4. Briefly, two linker probes were synthesised covering a 90 bp region spanning codons 507-520 and 520-533 of the MTB rpoB gene. Oligonucleotides were made using the cyanoethylphosphoramidite method. The two reporter domains of the probes are joined in each probe by a linker. The 3' end of each probe includes a blocker group. Note that the two linker probes cover adjoining regions of the genomic sequence. The probe sequences are:

```
rpoB (507>520) Linked-Probe
                                          (SEQ ID NO: 1)
(5'>3')
3GGGTTG1TCTGG1CCATGAATTGGCT*****CAGC1GGCTGG1GCCGAA
GAA2 rpoB (520>533) Linked-Probe
                                          (SEQ ID NO: 2)
(5'>3')
3CAGCGCCGACAG1CGGCG*****CT1GTGGG1CAACCCCGACAGC2
1 = fluorescein dT
2 = phosphate block
3 = trimethoxystilbene
* = Inosine residues (5 per probe)
```

Primers used for PCR amplification of target rpoB sequences from samples are shown below:

```
FWD primer v1
(5' > 3')
                                          (SEQ ID NO: 3)
GCAGACGTTGATCAACATCC FWD primer v2
(5' > 3')
                                          (SEQ ID NO: 4)
CGTGGAGGCGATCACACCGCAGACGTT.
```

Using these probes it is possible to detect the presence of mutations in a target sequence by virtue of changes in melting temperature arising from mismatches between the probe sequence and the target sequence. Single base mismatches can be detected with high sensitivity. See, for example, international patent application WO2013/041853, which describes use of similar probes (although only individual probes, not pairs of adjacent probes) to detect SNP mutations in the rpoB gene.

The labelled probe gave good amplification detection in both symmetric and asymmetric PCR (that is, where the labelled primer is non limiting, and where it is limiting). The detection of both peaks (ss and ds) allowed the transition threshold to be established; lowering the amount of limiting labelled primer could be used to lower the threshold (see melt curves in FIG. 3.1, showing a transition threshold of $>10^5$ template copy number, and $<10^5$ template copy number respectively).

Calculating the ratio of peak heights (dsDNA to ssDNA, see FIG. 3.2) gave a good approximation of the starting copy number over at least 5 logs to 100 copies of target model system. As can be seen, the log of the starting copy number is related to the peak height ratio in a linear manner. Therefore, determining the peak height ratio after an amplification reaction allows the starting copy number to be determined. The two separate lines on the graph represent data from linearity plots using 150 um and 250 um probe In this way, the use of a limiting primer to conduct asymmetric PCR, followed by comparison of the quantity of double stranded and single stranded product, is shown to provide a useful method to determine the amount of starting template. For example, a reaction could be run on a test sample, with a known amount of limiting primer. Once the desired ratio of dsDNA to ssDNA is reached, then the peak heights may be determined. The amount of dsDNA is governed by the amount of limiting primer, while the amount of ssDNA is proportional to the amount of starting template. Therefore the dsDNA peak may be used as a known quantity to determine the amount of ssDNA in the reaction. From this, the amount of starting template can be determined.

Although these examples illustrate a comparison of the concentration of limiting primer to the copy number of the starting template, the assay could equally (and more straightforwardly) compare the copy number of each or the concentration of each, given that the copy number of a given DNA sequence may be determined from the concentration, and vice versa.

A further illustration of the assay is shown in FIGS. 4-7. These show an example of the quantification of the amount of hepatitis C virus (HCV) in a sample. Asymmetric PCR was carried out on a series of samples of known starting copy number.

The primers and probe were as follows:

```
HCV-Fwd:
                                          (SEQ ID NO: 5)
5'-1GCTAGCCGAGTAGTGTTGGGT-3'

HCV-Rev:
                                          (SEQ ID NO: 6)
5'-TGCACGGTCTACGAGACCTCC
1 = TRIMETHOXYSTILBENE
Bold underlined = FLUORESCEIN dT
```

The forward primer was the limiting primer.

```
Viral Load Probe1:
                                              (SEQ ID NO: 7)
1GCCT5GTGGTAC5GCCTGAT66666AGGGTGCT5GCGAG5GCCCC3
1 = TMS (trimethoxystilbene)
5 = FLUORESCEIN dT
6 = Inosine
3 = propanol
```

The probe is a linker probe of the type described in WO2013/041853, in which the two segments are separated by polyinosine, and have discrete melting temperatures when hybridised to the target.

Reaction conditions and cycle times were as follows:

| Reagent | Final concentration (in 20 uL) |
|---|---|
| HCV-Forward Primer (5'TMS/FAM-labelled) | 0.1 uM |
| HCV-Reverse Probe | 1 uM |
| HCV-Probe | 0.2 uM |

Cycling Parameters

| Cycles | Conditions | | |
|---|---|---|---|
| 1 | 95° C. | 5 min | |
| 40 | 95° C. | 10 secs | |
| | 55° C. | 20 secs | |
| | 72° C. | 20 secs | |
| 1 | 95° C. | 5 sec | |
| | 40° C. | 1 min | |
| | 90° C. | 0 sec | acquisitions (5/degree) |
| 1 | 40° C. | 30 sec | |

Several assays were carried out with different starting quantities of the HCV template (HCV5 madrid plasmid).

Figure 4:
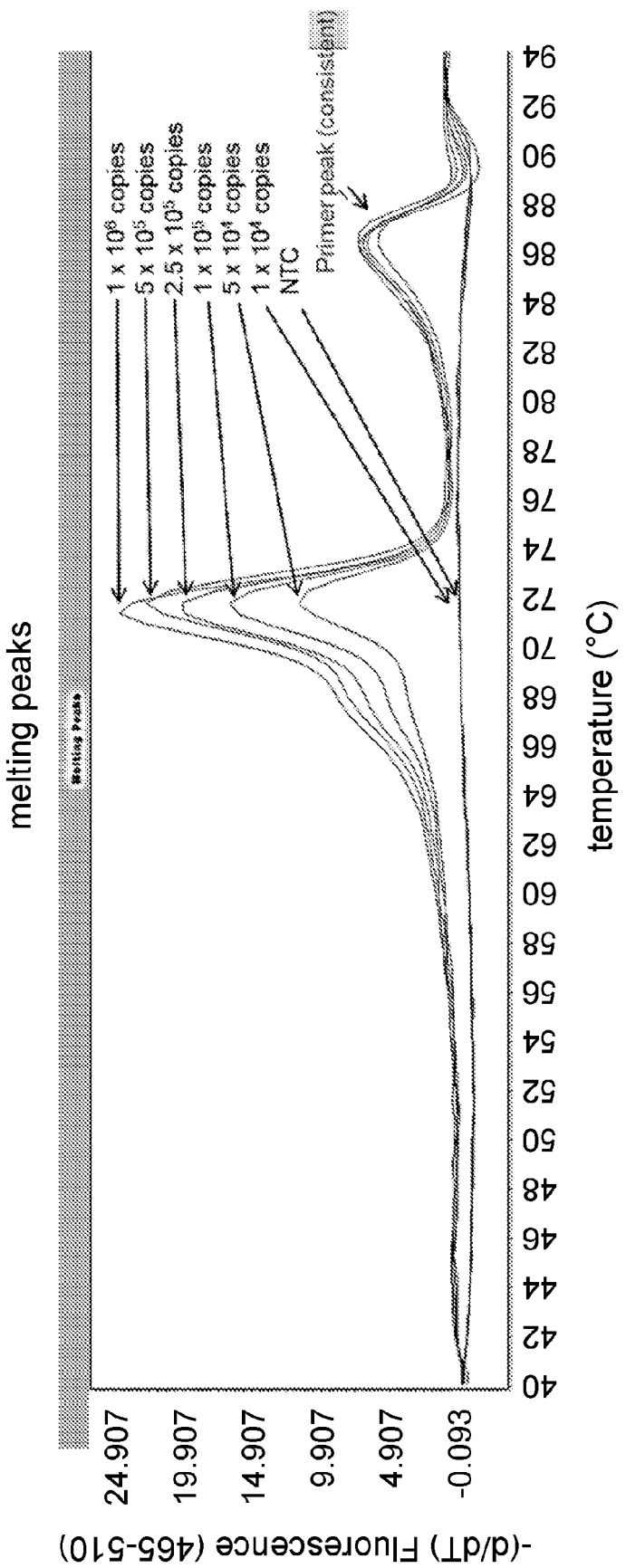
FIGS. 4 to 7 show results from a sample assay carried out for hepatitis C virus (HCV).
Figure 5B:
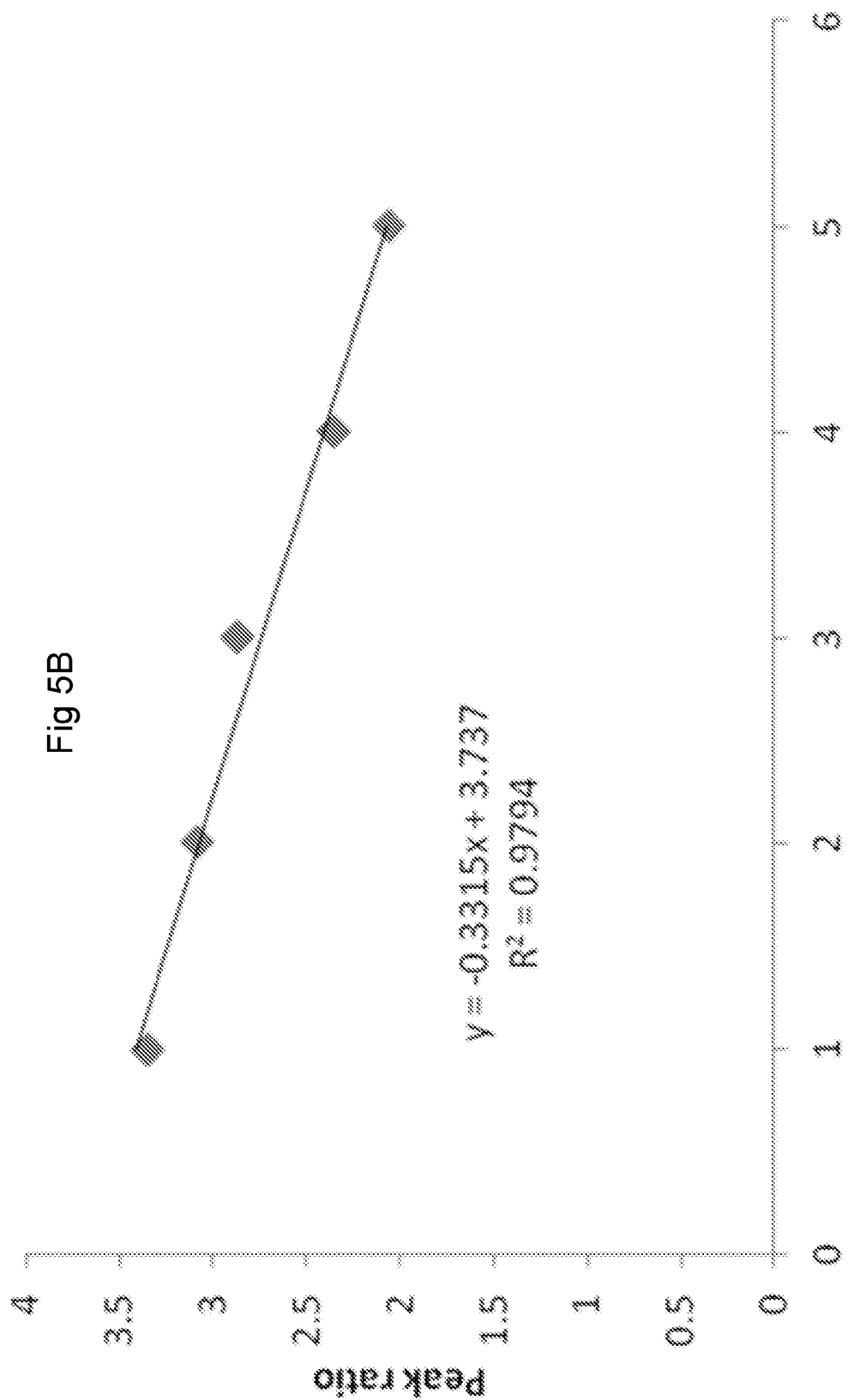
Figure 6A:
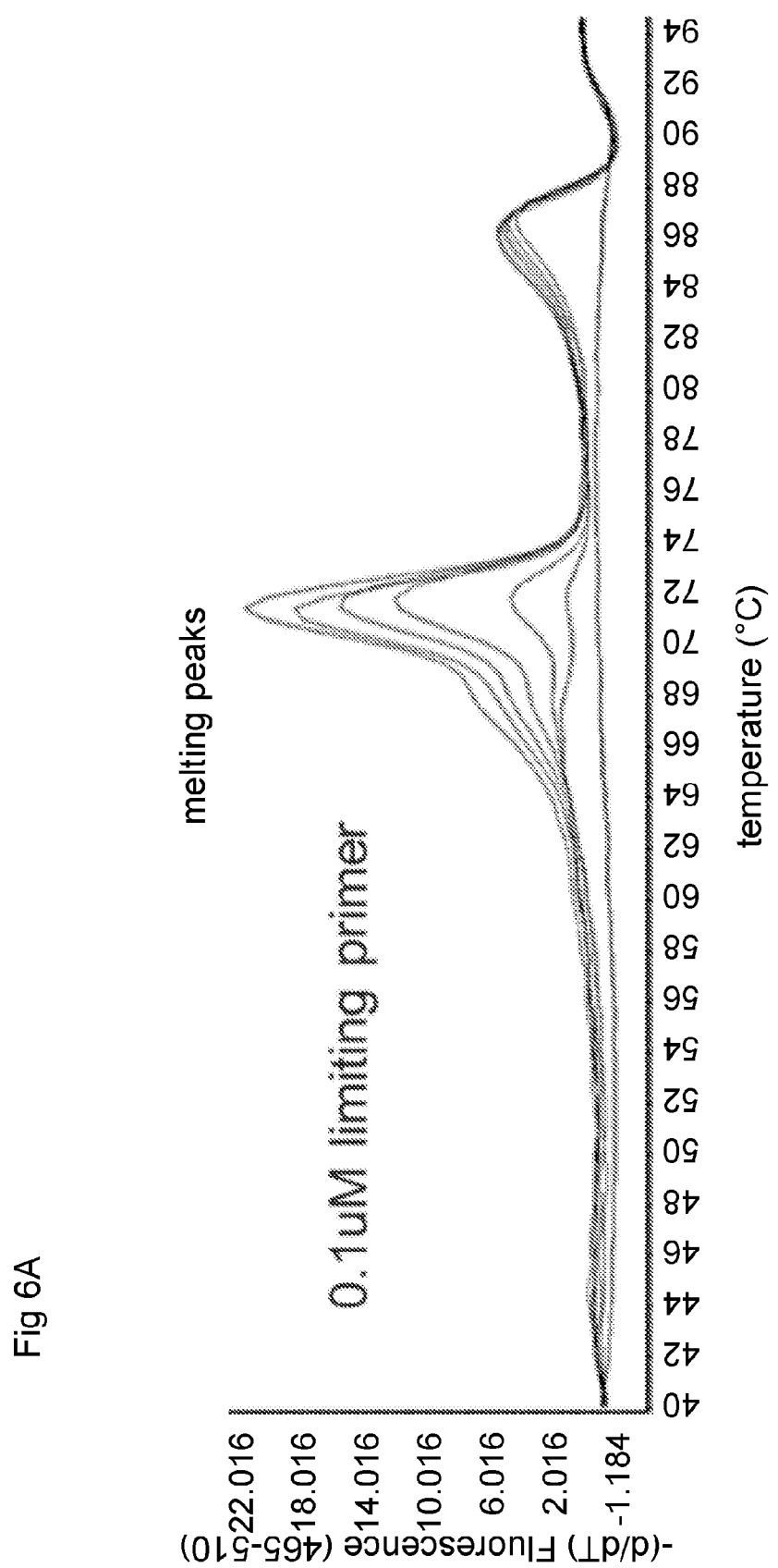
Figure 6B:
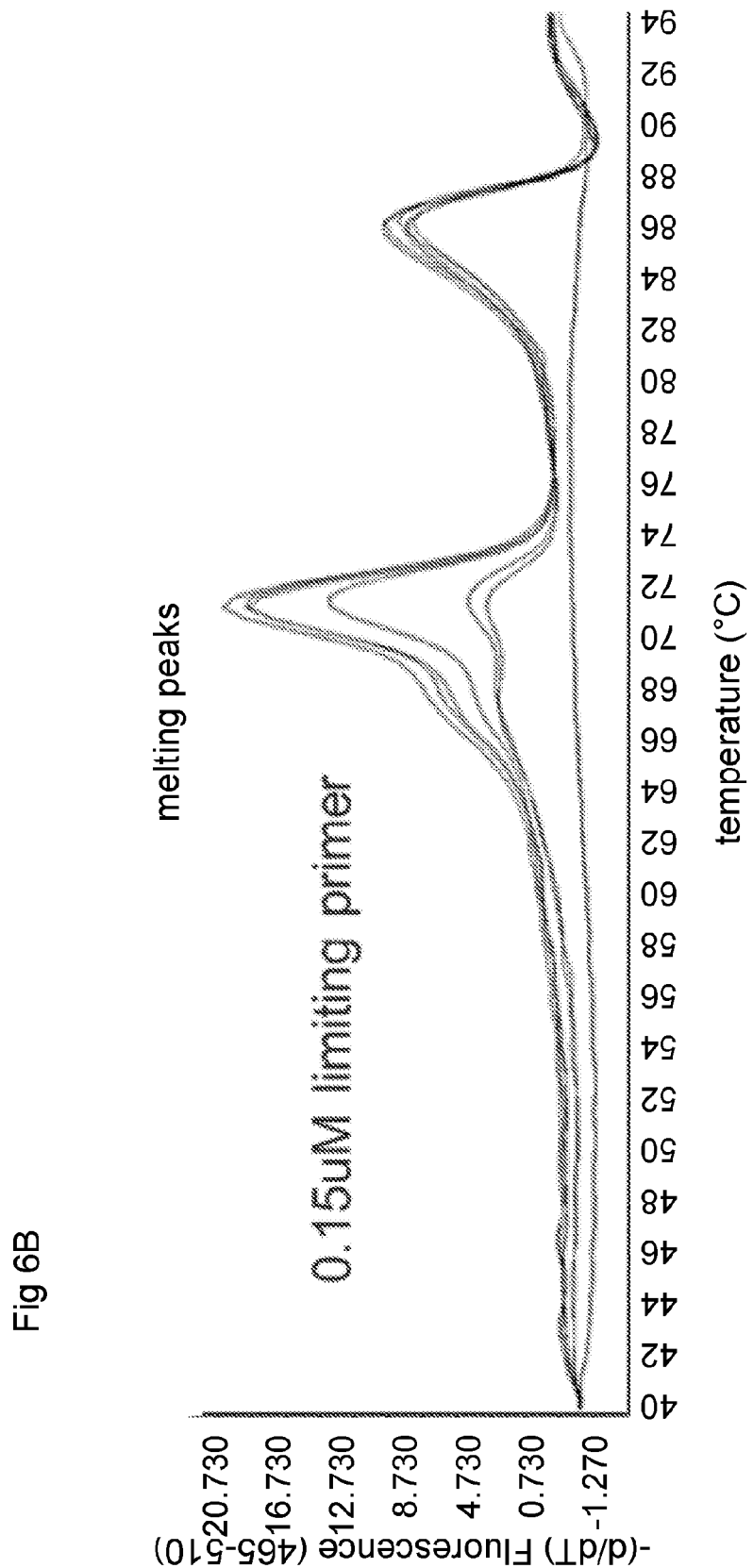
Figure 6C:
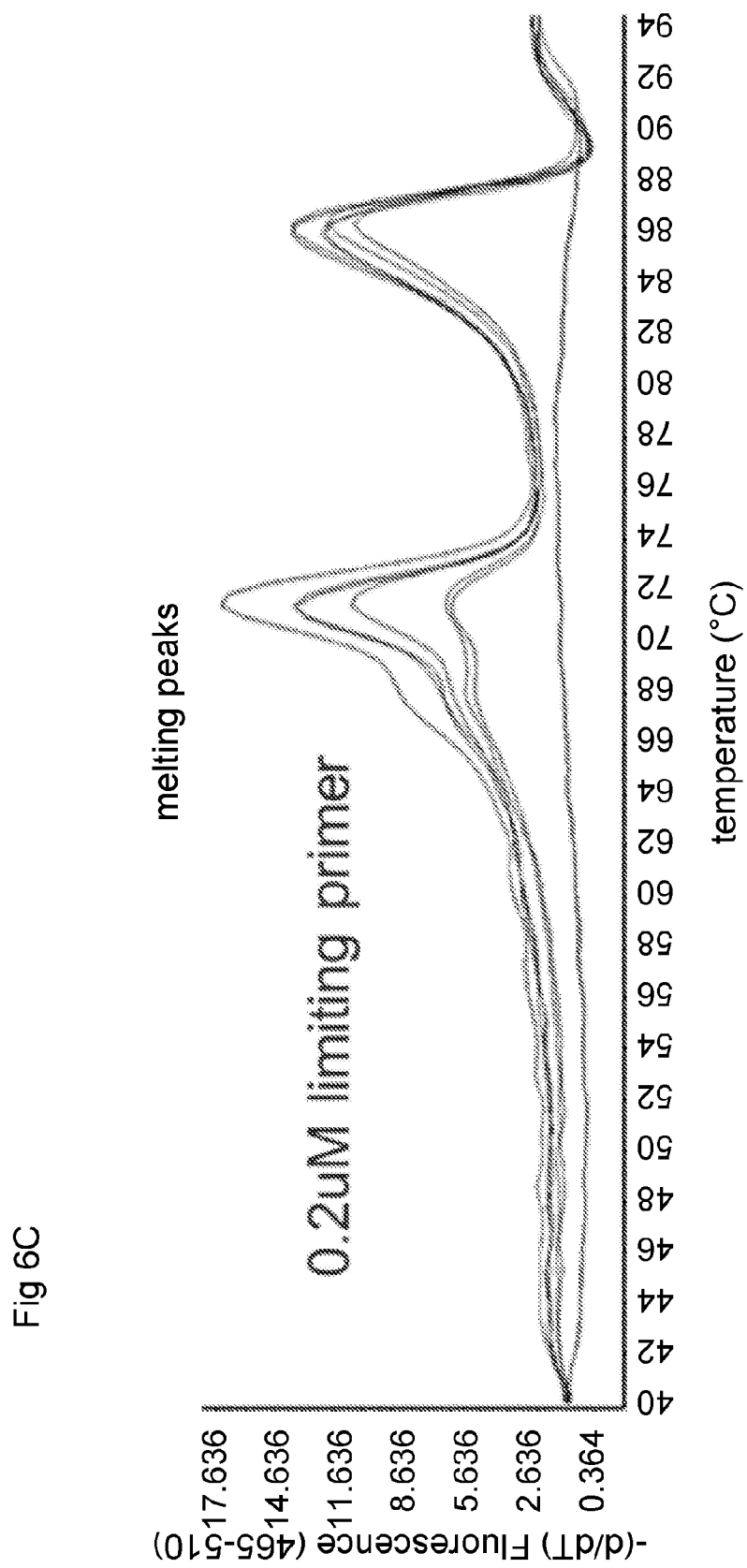
Figure 6D:
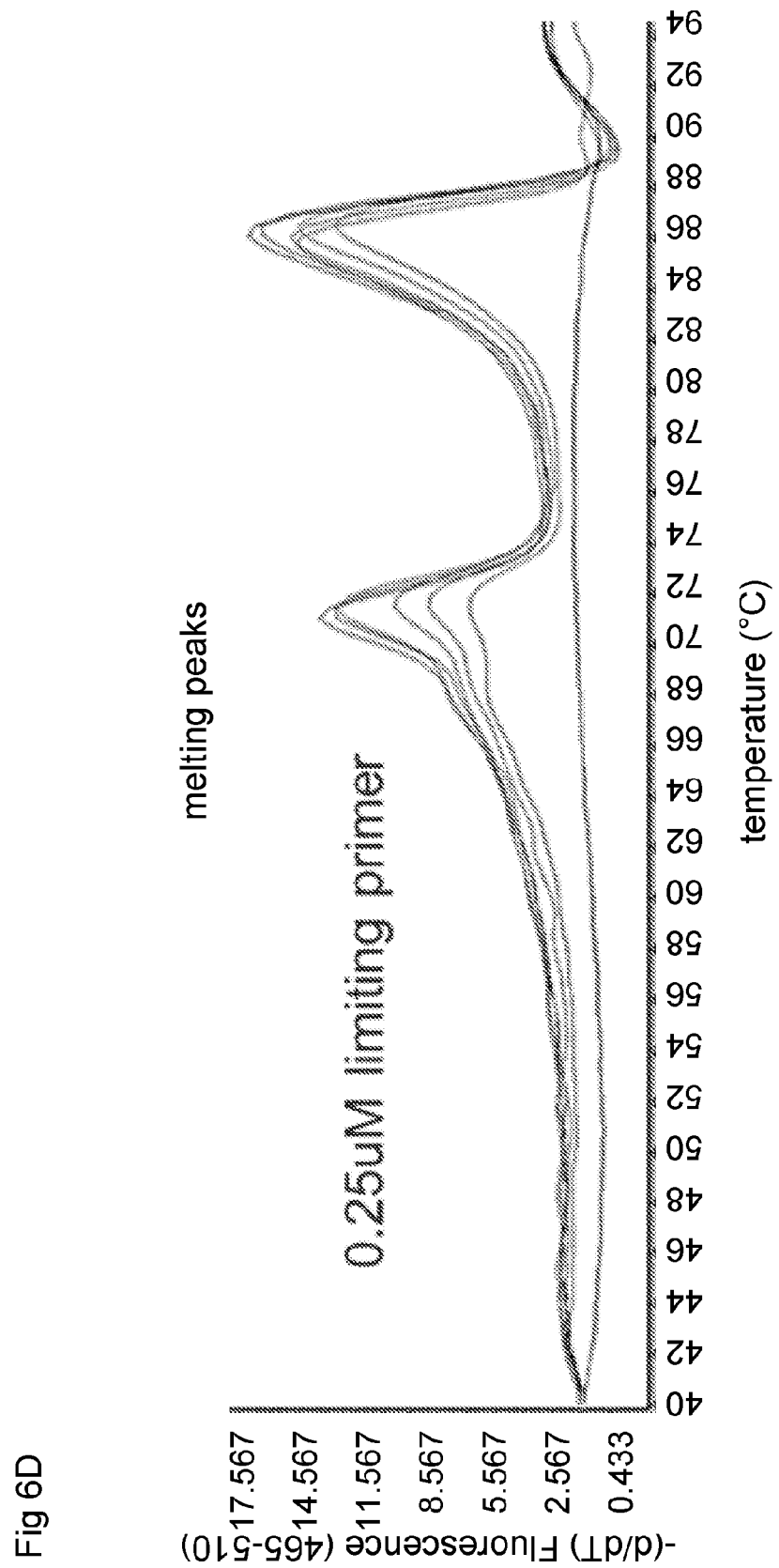

The results are shown in FIG. 4. This shows that the primer peak (ie, the peak which detects dsDNA incorporating the primer) is of constant height regardless of starting template, while the ssDNA peak varies in height depending on the amount of starting template (NTC=no template control). The relationship between starting template and ssDNA peak height is linear, see FIG. 5. This allows intra assay quantification, where the peak ratio may be used to determine the amount of starting template.

Figure 7A:
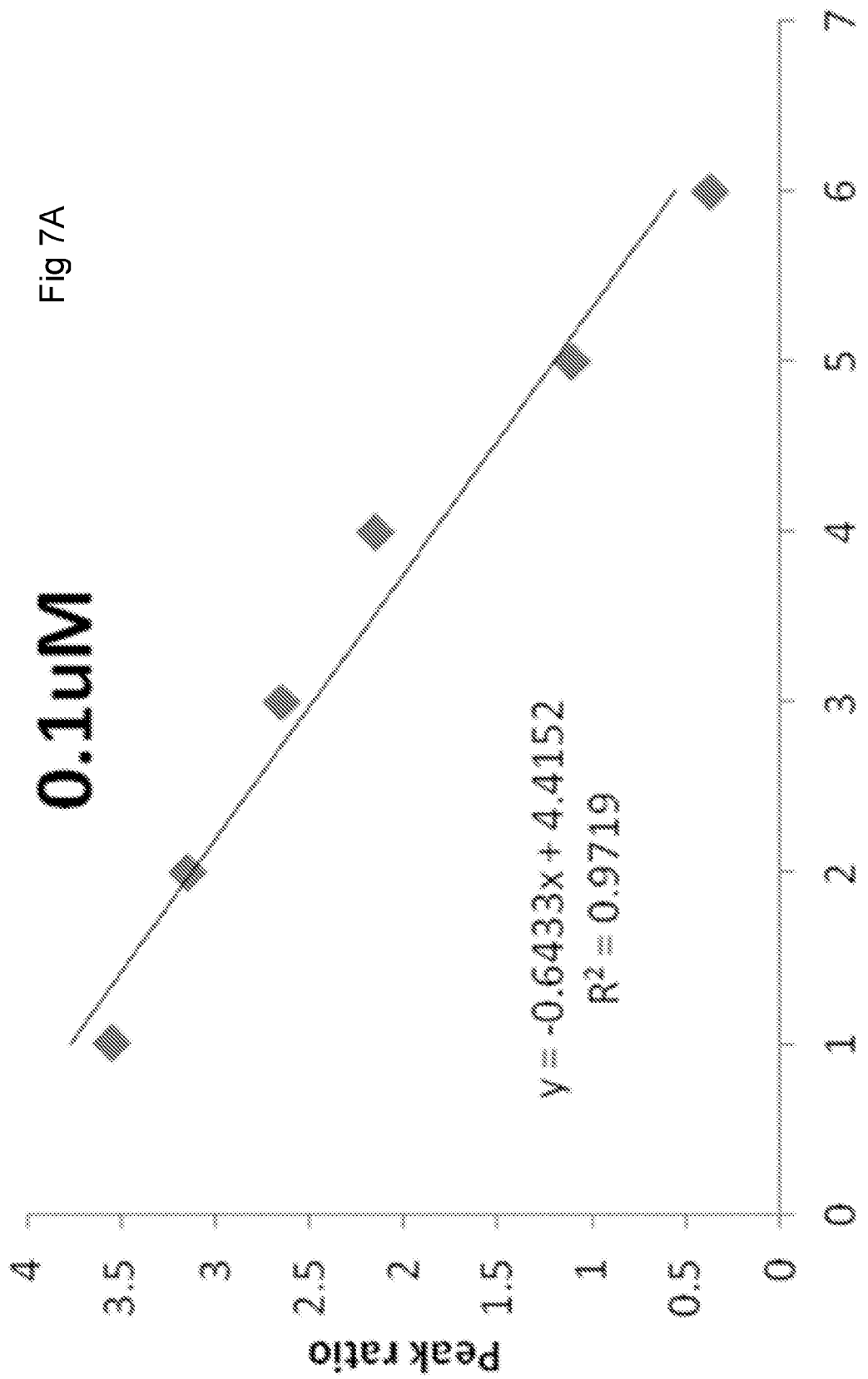
Figure 7C:
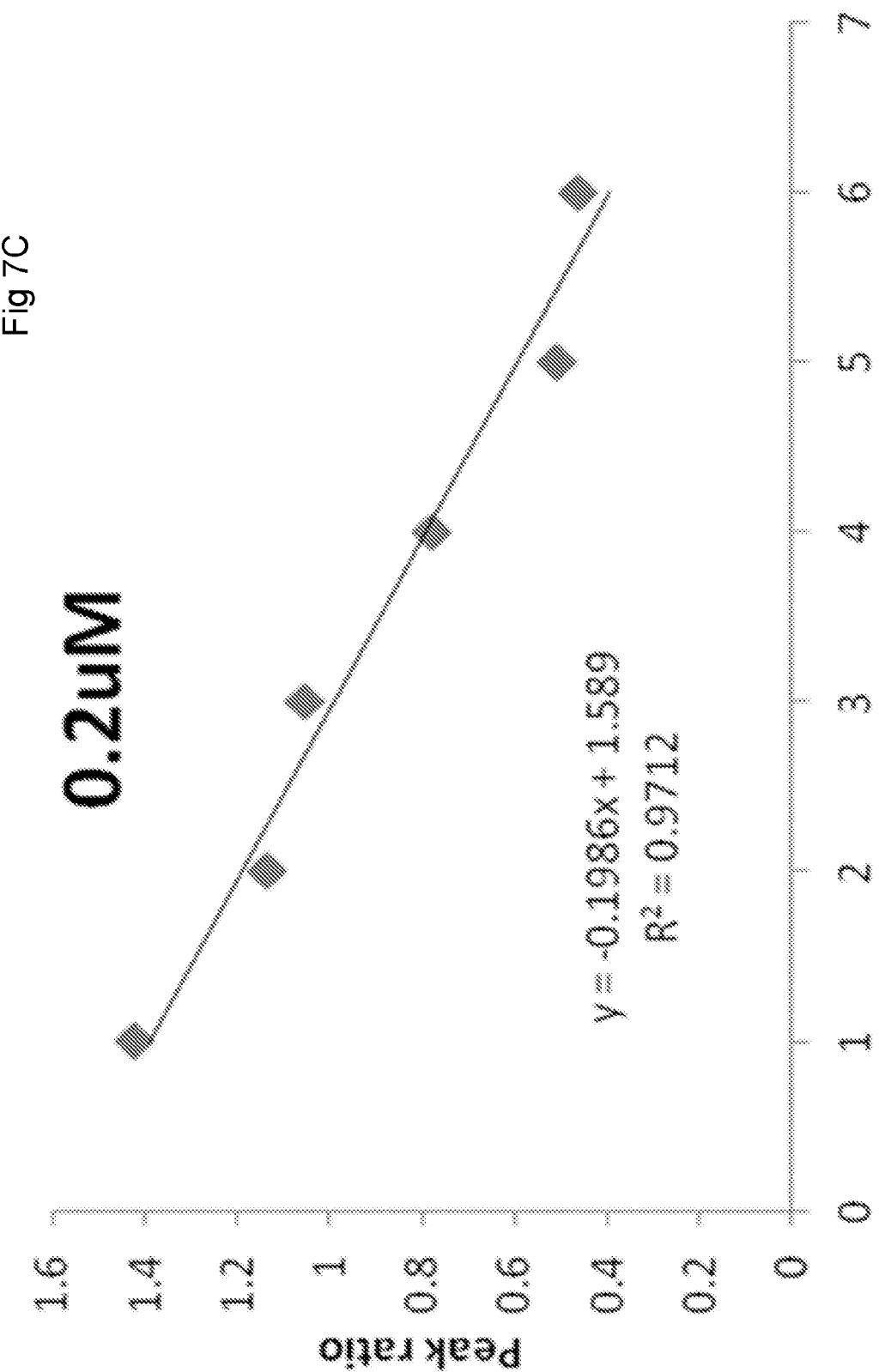
Figure 7D:
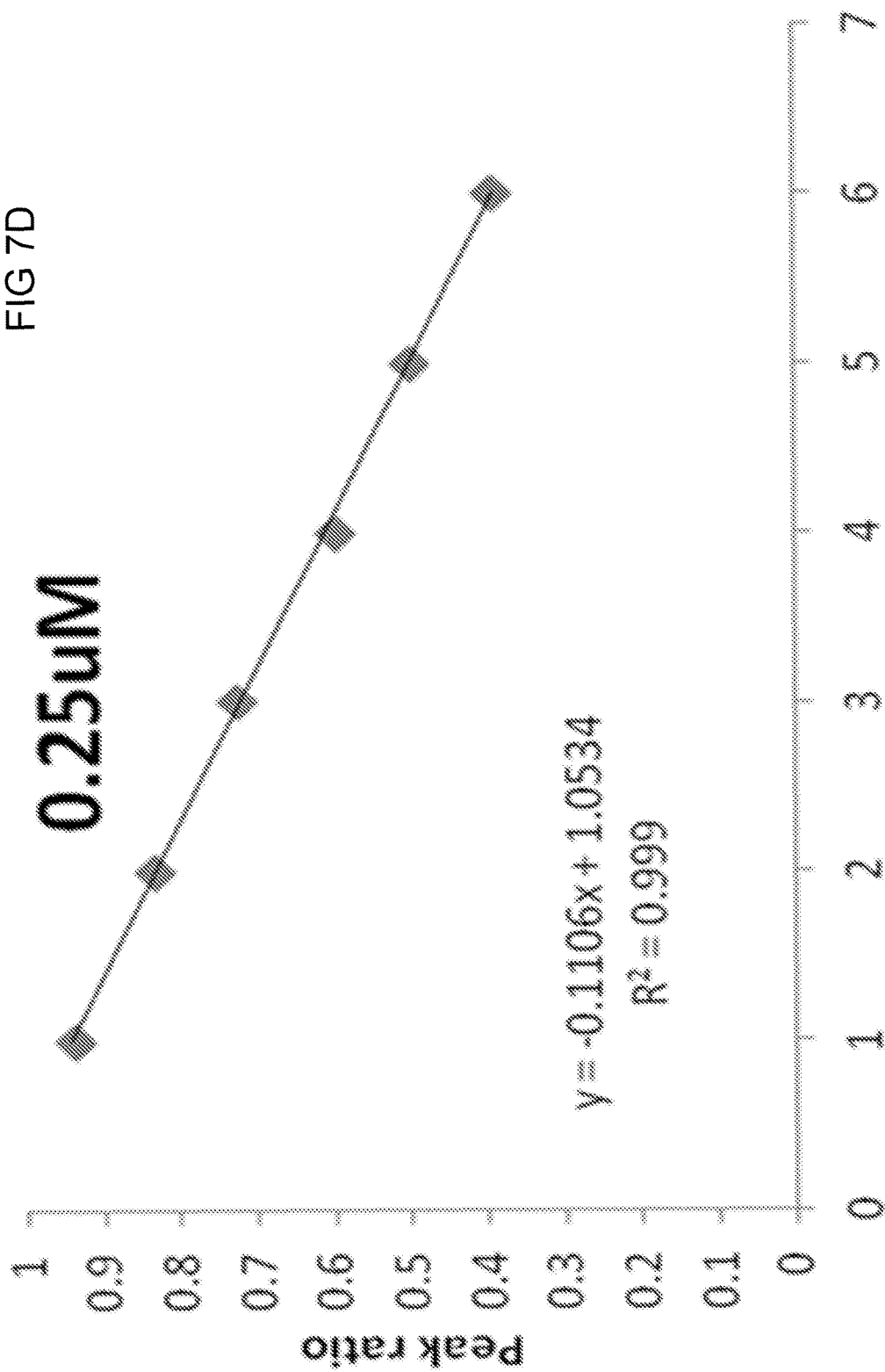

Adjusting the concentration of limiting primer results in progressive increase in size of the peak representing the labelled primer (equivalent to dsDNA), and reduction in target sequence intensity assayed by the probe. See FIG. 6. Where there is a lot of limiting primer (0.25 um in this example), the ratio of the dsDNA peak height to ssDNA peak height approaches close to one; however, as long as it remains less than one, the assay can still be used. In addition, the distinction between different starting amounts of target becomes narrower. The concentration of starting template used in these figures is the same as that used in FIG. 4; the other reaction conditions are also the same, apart from the limiting primer concentration. Regardless of the limiting primer concentration, as shown in FIG. 7, the linear relationship between log of the starting template copy number and peak ratio remains (the x axis is logarithmic). Note that in these figures, the ratio shown is of the ssDNA to dsDNA, not dsDNA to ssDNA shown in FIG. 3. Thus, for these results the desired ratio is greater than one; for certain values this ratio is not reached, for example 0.1 um limiting primer and $2.5 \times 100^{\wedge}4$ starting template. Nonetheless, the relationship holds. Importantly, although the limit of detection in these particular examples is relatively poor (low copy numbers give a ratio of ssDNA to dsDNA of less than one), this is a consequence of the particular assay design. The results serve to demonstrate the principle, which would be expected to hold for a range of alternative reaction conditions.

The invention claimed is:

1. A method for quantifying nucleic acid in a nucleic acid amplification reaction, the method comprising:

providing a template nucleic acid and first and second amplification primers, wherein the first primer is present in a limiting quantity;

performing an asymmetric nucleic acid amplification reaction under suitable conditions such that double stranded nucleic acid product is generated in an initial stage of the reaction, and single stranded nucleic acid product is generated in a subsequent stage of the reaction once the limiting first primer is exhausted;

providing a probe specific for the single stranded nucleic acid product, and allowing the probe to hybridize to single stranded product;

detecting relative amounts of double stranded nucleic acid product and single stranded nucleic acid product produced once the reaction has finished the subsequent stage by means of a melt curve analysis;

calculating the height of the double stranded product peak and the height of the single stranded product peak and determining whether the ratio of double stranded product peak height to single stranded product peak height is less than one; and if said ratio is less than one, then quantifying the amount of starting template based on the ratio of double stranded product peak height to single stranded product peak height, or if said ratio is greater than one, then discarding the reaction.

2. The method of claim 1 wherein the nucleic acid is DNA or cDNA.

3. The method of claim 1 wherein the amount of single stranded product is normalized with respect to the amount of double stranded product.

4. The method of claim 1 wherein, if the ratio of double stranded product to single stranded product is less than one, then the method further comprises using said ratio as an indicator of threshold cycle.

5. The method of claim 1 wherein method comprises determining the amounts of double stranded and single stranded product by dissociation or association curve analysis.

6. The method of claim 1 comprising introducing a detectable label to the reaction and detecting said label in order to determine relative amounts of single stranded and double stranded nucleic acid product.

7. The method of claim 6 wherein the label is a fluorescent dye which preferentially binds to double stranded nucleic acid.

8. The method of claim 6 wherein the detectable label comprises a label incorporated into the limiting primer.

9. The method of claim 6 wherein the label further comprises a fluorescent dye incorporated into the probe.

10. The method of claim 1 further comprising the step of predetermining the amount of the limiting primer, to provide a predetermined quantity of double stranded nucleic acid product.

11. The method of claim 10 wherein the amount of the limiting primer is predetermined to provide a ratio of double stranded product to single stranded product of between 1:15 and 1:5.

12. The method of claim 1 wherein the probe is a probe which can be used to distinguish between alleles of a target sequence; and further comprising the step of detecting hybridization of the probe to the single stranded product to determine the genotype of the template nucleic acid.

13. The method of claim 12 wherein the probe hybridizes to a first allele with a lower melting temperature (Tm) than that with which it hybridizes to a second allele.

14. The method of claim 12 wherein the probe has an anchor region and a reporter region separated by a linker nucleic acid sequence, the anchor and reporter regions having discrete melting temperatures.

* * * * *

SEQUENCE LISTING

```
<160> NUMBER OF SEQ ID NOS: 7

<210> SEQ ID NO 1
<211> LENGTH: 52
<212> TYPE: DNA
<213> ORGANISM: Artificial Sequence
<220> FEATURE:
<223> OTHER INFORMATION: Description of Artificial Sequence: Synthetic
      Linked-Probe
<220> FEATURE:
<223> OTHER INFORMATION: 5' trimethoxystilbene
<220> FEATURE:
<221> NAME/KEY: modified_base
<222> LOCATION: (7)..(7)
<223> OTHER INFORMATION: Fluorescein dT
<220> FEATURE:
<221> NAME/KEY: modified_base
<222> LOCATION: (13)..(13)
<223> OTHER INFORMATION: Fluorescein dT
<220> FEATURE:
<221> NAME/KEY: modified_base
<222> LOCATION: (27)..(31)
<223> OTHER INFORMATION: Inosine
<220> FEATURE:
<221> NAME/KEY: modified_base
<222> LOCATION: (36)..(36)
<223> OTHER INFORMATION: Fluorescein dT
<220> FEATURE:
<221> NAME/KEY: modified_base
<222> LOCATION: (43)..(43)
```

```
<223> OTHER INFORMATION: Fluorescein dT
<220> FEATURE:
<223> OTHER INFORMATION: 3' phosphate block

<400> SEQUENCE: 1
gggttgttct ggtccatgaa ttggctnnnn ncagctggct ggtgccgaag aa          52

<210> SEQ ID NO 2
<211> LENGTH: 45
<212> TYPE: DNA
<213> ORGANISM: Artificial Sequence
<220> FEATURE:
<223> OTHER INFORMATION: Description of Artificial Sequence: Synthetic
      Linked-Probe
<220> FEATURE:
<223> OTHER INFORMATION: 5' trimethoxystilbene
<220> FEATURE:
<221> NAME/KEY: modified_base
<222> LOCATION: (13)..(13)
<223> OTHER INFORMATION: Fluorescein dT
<220> FEATURE:
<221> NAME/KEY: modified_base
<222> LOCATION: (19)..(23)
<223> OTHER INFORMATION: Inosine
<220> FEATURE:
<221> NAME/KEY: modified_base
<222> LOCATION: (26)..(26)
<223> OTHER INFORMATION: Fluorescein dT
<220> FEATURE:
<221> NAME/KEY: modified_base
<222> LOCATION: (32)..(32)
<223> OTHER INFORMATION: Fluorescein dT
<220> FEATURE:
<223> OTHER INFORMATION: 3' phosphate block

<400> SEQUENCE: 2
cagcgccgac agtcggcgnn nnncttgtgg gtcaaccccg acagc                  45

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 3
gcagacgttg atcaacatcc                                              20

<210> SEQ ID NO 4
<211> LENGTH: 27
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 4
cgtggaggcg atcacaccgc agacgtt                                      27

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer
<220> FEATURE:
<223> OTHER INFORMATION: 5' trimethoxystilbene
<220> FEATURE:
<221> NAME/KEY: modified_base
```

-continued

```
<222> LOCATION: (11)..(11)
<223> OTHER INFORMATION: Fluorescein dT
<220> FEATURE:
<221> NAME/KEY: modified_base
<222> LOCATION: (16)..(16)
<223> OTHER INFORMATION: Fluorescein dT

<400> SEQUENCE: 5
gctagccgag tagtgttggg t                                        21

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 6
tgcacggtct acgagacctc c                                        21

<210> SEQ ID NO 7
<211> LENGTH: 45
<212> TYPE: DNA
<213> ORGANISM: Artificial Sequence
<220> FEATURE:
<223> OTHER INFORMATION: Description of Artificial Sequence: Synthetic
      Probe
<220> FEATURE:
<223> OTHER INFORMATION: 5' trimethoxystilbene
<220> FEATURE:
<221> NAME/KEY: modified_base
<222> LOCATION: (5)..(5)
<223> OTHER INFORMATION: Fluorescein dT
<220> FEATURE:
<221> NAME/KEY: modified_base
<222> LOCATION: (13)..(13)
<223> OTHER INFORMATION: Fluorescein dT
<220> FEATURE:
<221> NAME/KEY: modified_base
<222> LOCATION: (21)..(25)
<223> OTHER INFORMATION: Inosine
<220> FEATURE:
<221> NAME/KEY: modified_base
<222> LOCATION: (34)..(34)
<223> OTHER INFORMATION: Fluorescein dT
<220> FEATURE:
<221> NAME/KEY: modified_base
<222> LOCATION: (40)..(40)
<223> OTHER INFORMATION: Fluorescein dT
<220> FEATURE:
<223> OTHER INFORMATION: 3' propanol

<400> SEQUENCE: 7
gccttgtggt actgcctgat nnnnnagggt gcttgcgagt gcccc              45
```